(12) United States Patent
Grasso et al.

(10) Patent No.: US 10,369,352 B2
(45) Date of Patent: Aug. 6, 2019

(54) REPRODUCIBLE PLACEMENT OF ABI ELECTRODES

(71) Applicant: MED-EL Elektromedizinische Geraete GmbH, Innsbruck (AT)

(72) Inventors: Peter Grasso, Innsbruck (AT); Stefan Brill, Munich (DE)

(73) Assignee: MED-EL Elektromedizinische Geraete GmbH, Inssbruck (AT)

( * ) Notice: Subject to any disclaimer, the term of this patent is extended or adjusted under 35 U.S.C. 154(b) by 302 days.

(21) Appl. No.: 15/423,678

(22) Filed: Feb. 3, 2017

(65) Prior Publication Data
US 2017/0224980 A1     Aug. 10, 2017

Related U.S. Application Data

(60) Provisional application No. 62/291,553, filed on Feb. 5, 2016, provisional application No. 62/291,556, filed on Feb. 5, 2016.

(51) Int. Cl.
*A61N 1/05* (2006.01)
*A61B 5/04* (2006.01)
(Continued)

(52) U.S. Cl.
CPC ........ *A61N 1/0529* (2013.01); *A61B 5/04001* (2013.01); *A61B 5/12* (2013.01);
(Continued)

(58) Field of Classification Search
CPC .. A61N 1/0526; A61N 1/0529; A61N 1/0531; A61N 1/0541; A61N 1/36036;
(Continued)

(56) References Cited

U.S. PATENT DOCUMENTS

| 9,795,785 B2 * | 10/2017 | Schwarz | A61N 1/36039 |
| 2008/0300652 A1 * | 12/2008 | Lim | A61N 1/36036 |
| | | | 607/56 |

(Continued)

OTHER PUBLICATIONS

Carvalho et al. Far Lateral Surgical Approach for Auditory Brainstem Implant in Neurofibromatosis, Type 2,Journal of Otolaryngology-ENT Research, vol. 3, Issue 5, 2015, 6 pages.
(Continued)

*Primary Examiner* — Eugene T Wu
(74) *Attorney, Agent, or Firm* — Sunstein Kann Murphy & Timbers LLP

(57) ABSTRACT

A method is described for determining an optimal placement location for an auditory brainstem implant (ABI) electrode array. A cochlear implant (CI) electrode array is inserted into a patient cochlea, and the ABI electrode array is initially placed at an initial placement location on a patient brainstem. The optimal placement location for the ABI electrode array is then determined by, for multiple electrode contacts on the ABI electrode array: i. selecting a specific electrode contact, ii. delivering a stimulation signal to the selected electrode contact, iii. sensing an efferent nerve signal from the stimulation signal using the electrode contacts of the CI electrode array, and iv. determining a maximum response location in the patient cochlea where a largest efferent nerve signal is sensed. The ABI electrode array is then repositioned to the optimal placement location.

20 Claims, 8 Drawing Sheets

(51) Int. Cl.
*A61B 5/00* (2006.01)
*A61B 5/12* (2006.01)
*A61N 1/36* (2006.01)

(52) U.S. Cl.
CPC .......... *A61B 5/4064* (2013.01); *A61B 5/6868* (2013.01); *A61N 1/0541* (2013.01); *A61N 1/36036* (2017.08); *A61N 1/36038* (2017.08)

(58) Field of Classification Search
CPC ............ A61N 1/36038; A61N 1/36039; A61N 1/3605; A61N 1/36057; A61N 1/3606; A61N 1/37241; A61B 5/04; A61B 5/04001; A61B 5/12; A61B 5/121; A61B 5/125; A61B 5/40; A61B 5/4005; A61B 5/4052; A61B 5/4058; A61B 5/4064; A61B 5/4851; A61B 5/6867; A61B 5/6868
See application file for complete search history.

(56) References Cited

U.S. PATENT DOCUMENTS

| | | | |
|---|---|---|---|
| 2012/0197153 A1* | 8/2012 | Kraus | A61B 5/04845 600/545 |
| 2013/0296969 A1 | 11/2013 | Swanson | |
| 2014/0243714 A1 | 8/2014 | Ward et al. | |
| 2015/0342505 A1 | 12/2015 | Lodwig et al. | |

OTHER PUBLICATIONS

Lin et al. Central masking with bilateral cochlear implants, J. Acoust. Soc. Am. vol. 133, No. 2, Feb. 2013, pp. 962-969.
International Searching Authority International Search Report—International Application No. PCT/US17/16335, dated Jun. 21, 2017, together with the Written Opinion of the International Searching Authority, 18 pages.

\* cited by examiner

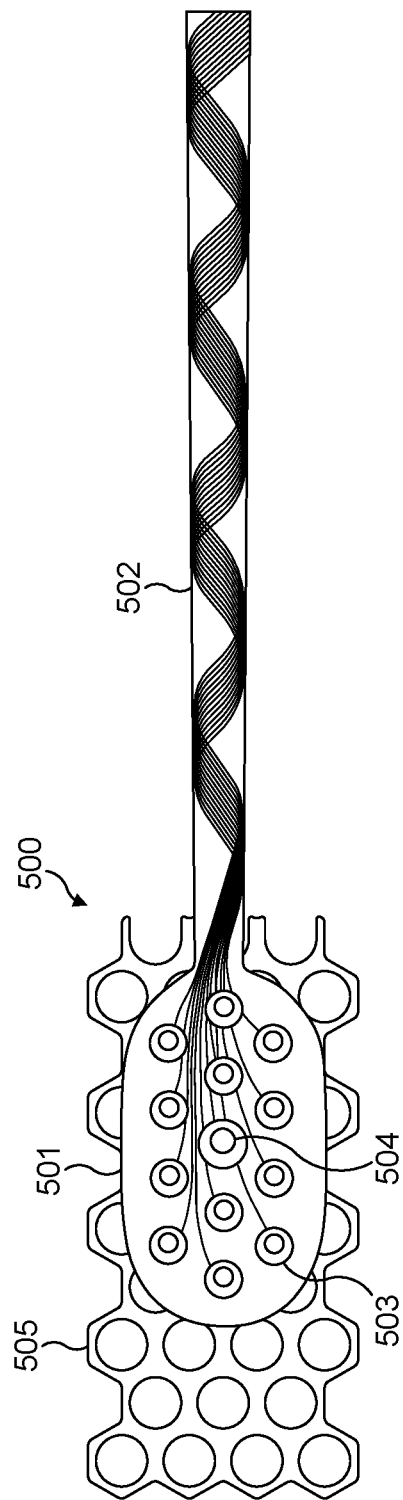

REPRODUCIBLE PLACEMENT OF ABI ELECTRODES

This application claims priority from U.S. Provisional Patent Application 62/291,553, filed Feb. 5, 2016, and from U.S. Provisional Patent Application 62/291,556, filed Feb. 5, 2016, both of which are incorporated herein by reference in their entireties.

FIELD OF THE INVENTION

The present invention relates to hearing implant systems, and more specifically, to techniques for determining an optimal location for an auditory brainstem implant electrode.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

FIG. 2 shows various functional blocks in a signal processing arrangement for producing electrode stimulation signals to electrode contacts in an implanted cochlear implant array according to a typical hearing implant system. A pseudo code example of such an arrangement can be set forth as:

Input Signal Preprocessing:
    BandPassFilter (input_sound, band_pass_signals)
Envelope Extraction:
    BandPassEnvelope (band_pass_signals, band_pass_envelopes)
Stimulation Timing Generation:
    TimingGenerate (band_pass_signals, stim_timing)
Pulse Generation:
    PulseGenerate (band_pass_envelopes, stim_timing, out_pulses)

The details of such an arrangement are set forth in the following discussion.

In the arrangement shown in FIG. 2, the initial input sound signal is produced by one or more sensing microphones, which may be omnidirectional and/or directional. Preprocessor Filter Bank 201 pre-processes this input sound signal with a bank of multiple parallel band pass filters (e.g. Infinite Impulse Response (IIR) or Finite Impulse Response (FIR)), each of which is associated with a specific band of audio frequencies, for example, using a filter bank with 12 digital Butterworth band pass filters of 6th order, Infinite Impulse Response (IIR) type, so that the acoustic audio signal is filtered into some K band pass signals, $U_1$ to $U_K$ where each signal corresponds to the band of frequencies for one of the band pass filters. Each output of sufficiently narrow CIS band pass filters for a voiced speech input signal may roughly be regarded as a sinusoid at the center frequency of the band pass filter which is modulated by the envelope signal. This is also due to the quality factor ($Q\approx3$) of the filters. In case of a voiced speech segment, this envelope is approximately periodic, and the repetition rate is equal to the pitch frequency. Alternatively and without limitation, the Preprocessor Filter Bank 201 may be implemented based on use of a fast Fourier transform (FFT) or a short-time Fourier transform (STFT). Based on the tonotopic organization of the cochlea, each electrode contact in the scala tympani typically is associated with a specific band pass filter of the Preprocessor Filter Bank 201. The Preprocessor Filter Bank 201 also may perform other initial signal processing functions such as and without limitation automatic gain control (AGC) and/or noise reduction and/or wind noise reduction and/or beamforming and other well-known signal enhancement functions.

FIG. 3 shows an example of a short time period of an input speech signal from a sensing microphone, and FIG. 4 shows the microphone signal decomposed by band-pass filtering by a bank of filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

The band pass signals $U_1$ to $U_K$ (which can also be thought of as electrode channels) are output to an Envelope Detector 202 and Fine Structure Detector 203. The Envelope Detector 202 extracts characteristic envelope signals outputs $Y_1, \ldots, Y_K$ that represent the channel-specific band pass envelopes. The envelope extraction can be represented by $Y_k$=LP($|U_k|$), where $|.|$ denotes the absolute value and LP(.) is a low-pass filter; for example, using 12 rectifiers and 12 digital Butterworth low pass filters of 2nd order, IIR-type. Alternatively, the Envelope Detector 202 may extract the Hilbert envelope, if the band pass signals $U_1, \ldots, U_K$ are generated by orthogonal filters.

The Fine Structure Detector 203 functions to obtain smooth and robust estimates of the instantaneous frequencies in the signal channels, processing selected temporal fine structure features of the band pass signals $U_1, \ldots, U_K$ to generate stimulation timing signals $X_1, \ldots, X_K$. The band pass signals $U_1, \ldots, U_k$ can be assumed to be real valued signals, so in the specific case of an analytic orthogonal filter bank, the Fine Structure Detector 203 considers only the real valued part of $U_k$. The Fine Structure Detector 203 is formed of K independent, equally-structured parallel sub-modules.

The extracted band-pass signal envelopes $Y_1, \ldots, Y_K$ from the Envelope Detector 202, and the stimulation timing signals $X_1, \ldots, X_K$ from the Fine Structure Detector 203 are input signals to a Pulse Generator 204 that produces the electrode stimulation signals Z for the electrode contacts in the implanted electrode array 205. The Pulse Generator 204 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 204 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

While the foregoing discussion of cochlear implant systems covers many persons suffering from impaired hearing, some patients suffer from growth of a tumor in close vicinity to the auditory nerve; e.g. in patients with Neurofibromatosis Type II (NF2). This tumor has to be surgically removed, and in most cases, the auditory nerve also is removed together with the tumor. In some such cases, the auditory nerve may remain partially intact, but within a period of time after surgery, it loses the ability to transmit action potentials elicited in the cochlear to the brainstem. Consequently, such patients are either deaf immediately after the surgery, or they become deaf some time later. For many such patients, hearing can be restored by an auditory brainstem implant (ABI).

The main structural difference between a cochlear implant (CI) system and an ABI system is in the form of the implanted electrode array. FIG. 5 shows an example of an ABI electrode array 500 which has an electrode lead 502 containing wires that deliver the electrical stimulation signals to electrode contacts 503 and a reference contact 504 on an electrode paddle 501 that is located at the distal end of the electrode lead 502. A polyester paddle mesh 505 supports the electrode paddle 501 which is placed against the brainstem of the implanted patient.

While ABI systems have proven to be a great help providing hearing perception for the patients who receive them, it is well known that they suffer from some shortcomings as compared to cochlear implants. For example, tonotopicity in the brainstem is less pronounced than in the cochlea. As a result, much more effort and time (longer surgery) is needed to find an optimal location for the electrode contacts on the ABI electrode array. Moreover, while the tonotopicity in the cochlea is one-dimensional along the longitudinal extension of its scalae, in the brainstem the tonotopicity is distributed over a two-dimensional area (at least, it may be even considered over a three-dimensional space region in the brainstem because the addressable brainstem region for this purpose is not only at the surface).

At present, a good placement of the ABI electrode array is based on electrically evoked auditory brainstem responses (EABR) that are measured during the surgery (when the patient is not able to give subjective feedback because of the anesthesia). However, EABR measurements are not frequency specific, and therefore, they provide only limited help with the placement of the electrode array. Because of the foregoing, it is often the case that hearing perception by ABI patients is usually worse than for CI patients.

Auditory sensing via the cochlea is an example of an afferent nerve sensing pathway. Afferent neurons act as sensing mechanisms that direct sensing signals from different parts of the body towards the brain, providing the brain with information about the condition of that body location. By contrast, efferent nerve pathways operate in the other direction, from the brain to a remote body location, to initiate some action. There is an efferent nerve path from the brain to the cochlea, known as the olivocochlear system. These efferent neurons terminate at the inner (medial) hair cells and the outer (lateral) hair cells within the cochlea to create mechanical action. Commonly understood functions of this arrangement include protection against loud sounds, improving signal to noise ratio, frequency selectivity, and processing of interaural time and phase differences.

Otoacoustic emissions are sounds that originate in the cochlea due to motion of the sensory hair cells within the cochlea as they respond to auditory stimulation. Otoacoustic emissions propagate out from the oval window membrane through the middle ear and across the tympanic membrane into the ear canal. Otoacoustic emissions are detectable by an sensitive microphone placed in the middle ear or ear canal, and they currently are used as the basis testing for hearing defects in newborn babies.

SUMMARY OF THE INVENTION

Embodiments of the present invention are directed to a method and corresponding non-transitory tangible computer-readable medium having instructions thereon for determining an optimal placement location for an auditory brainstem implant (ABI) electrode array having multiple electrode contacts configured for delivering electrical stimulation signals. A cochlear implant (CI) electrode array having a plurality of electrode contacts configured for delivering electrical stimulation signals to adjacent neural tissue is inserted into a patient cochlea. The ABI electrode array is initially placed at an initial placement location on a patient brainstem. An improved placement location for the ABI electrode array is determined by, for multiple electrode contacts on the CI electrode array: i. selecting a specific electrode contact of the CI electrode array, ii. delivering a stimulation signal to the selected electrode contact, iii. sensing an afferent nerve signal response to the stimulation signal using the electrode contacts of the ABI electrode array, and iv. determining a maximum response location on the patient brainstem where a largest afferent nerve signal is sensed. The ABI electrode array is then repositioned to the improved placement location. The optimal placement location is then determined for the ABI electrode array by, for multiple electrode contacts on the ABI electrode array: i. selecting a specific electrode contact of the ABI electrode array, ii. delivering a stimulation signal to the selected electrode contact, iii. sensing an efferent nerve signal response to the stimulation signal using the electrode contacts of the CI electrode array, and iv. determining a maximum response location in the patient cochlea where a largest efferent nerve signal is sensed. The ABI electrode array is then repositioned to the optimal placement location.

In further specific embodiments, the steps of determining the improved placement location and repositioning the ABI electrode array may be reperformed. Similarly, the steps of determining the optimal placement location and repositioning the ABI electrode array may be reperformed. The stimulation signal delivered to the selected electrode contact may be a single electrical pulse, or a sequence of multiple electrical pulses. Determining the improved placement location for the ABI electrode array may include using all of the electrode contacts on the CI electrode array and/or determining the optimal placement location for the ABI electrode array may include using all of the electrode contacts on the ABI electrode array. Sensing the afferent nerve signal response may include sensing a late elaboration of the afferent nerve signal response to the stimulation signal such as an electrically evoked auditory brainstem response (EABR) signal.

Embodiments of the present invention also include a method for determining an optimal placement location for an auditory brainstem implant (ABI) electrode array. A cochlear implant (CI) electrode array is inserted into a patient cochlea. The ABI electrode array is initially placed at an initial placement location on a patient brainstem. The optimal placement location for the ABI electrode array is then determined by, for multiple electrode contacts on the ABI electrode array: i. selecting a specific electrode contact of the ABI electrode array, ii. delivering a stimulation signal to the selected electrode contact, iii. sensing an efferent nerve signal from the stimulation signal using the electrode contacts of the CI electrode array, and iv. determining a maximum response location in the patient cochlea where a largest efferent nerve signal is sensed. The ABI electrode array is then repositioned to the optimal placement location.

Embodiments of the present invention also include a method for determining an optimal placement location for an auditory brainstem implant (ABI) electrode array. A cochlear implant (CI) electrode array is inserted into a patient cochlea. The ABI electrode array is initially placed at an initial placement location on a patient brainstem. The optimal placement location for the ABI electrode array is then determined by, for a plurality of electrode contacts on the CI electrode array: i. selecting a specific electrode contact of the CI electrode array, ii. delivering a stimulation signal to the selected electrode contact, iii. sensing an afferent nerve signal response to the stimulation signal using the electrode contacts of the ABI electrode array, and iv. determining a maximum response location on the patient brainstem where a largest afferent nerve signal is sensed. The ABI electrode array is then repositioned to the optimal placement location.

Embodiments of the present invention are directed to a method and corresponding non-transitory tangible computer-readable medium having instructions thereon for determining an optimal placement location for an auditory brainstem implant (ABI) electrode array having multiple electrode contacts configured for delivering electrical stimulation signals. The ABI electrode array is initially placed at an initial placement location on a patient brainstem. An improved placement location for the ABI electrode array is determined by, for multiple acoustic stimulus frequencies: i. selecting a specific acoustic stimulus frequency, ii. delivering an acoustic stimulus at the selected acoustic stimulus frequency, iii. sensing an afferent nerve signal response to the acoustic stimulus using the electrode contacts of the ABI electrode array, and iv. determining a maximum response location on the patient brainstem where a largest afferent nerve signal is sensed. The ABI electrode array is then repositioned to the improved placement location. The optimal placement location is then determined for the ABI electrode array by, for multiple electrode contacts on the ABI electrode array: i. selecting a specific electrode contact of the ABI electrode array, ii. delivering a stimulation signal to the selected electrode contact, iii. sensing an otoacoustic emission response to the stimulation signal, and iv. determining a frequency and intensity of the otoacoustic emission response. The ABI electrode array is then repositioned to the optimal placement location.

In further specific embodiments, the steps of determining the improved placement location and repositioning the ABI electrode array may be reperformed. Similarly, the steps of determining the optimal placement location and repositioning the ABI electrode array may be reperformed. The stimulation signal delivered to the selected electrode contact may be a single electrical pulse, or a sequence of multiple electrical pulses. Determining the optimal placement location for the ABI electrode array may include using all of the electrode contacts on the ABI electrode array. Sensing the afferent nerve signal response may include sensing a late elaboration of the afferent nerve signal response to the stimulation signal such as an electrically evoked auditory brainstem response (EABR) signal.

Embodiments of the present invention also include a method for determining an optimal placement location for an auditory brainstem implant (ABI) electrode array. The ABI electrode array is initially placed at an initial placement location on a patient brainstem. The optimal placement location for the ABI electrode array is then determined by, for multiple electrode contacts on the ABI electrode array: i. selecting a specific electrode contact of the ABI electrode array, ii. delivering a stimulation signal to the selected electrode contact, iii. sensing an otoacoustic emission response to the stimulation signal, and iv. determining a frequency and intensity of the otoacoustic emission response. The ABI electrode array is then repositioned to the optimal placement location.

Embodiments of the present invention also include a method for determining an optimal placement location for an auditory brainstem implant (ABI) electrode array. The ABI electrode array is initially placed at an initial placement location on a patient brainstem. The optimal placement location for the ABI electrode array is then determined by, for a plurality of acoustic stimulus frequencies: i. selecting a specific acoustic stimulus frequency, ii. delivering an acoustic stimulus at the selected acoustic stimulus frequency, iii. sensing an afferent nerve signal response to the stimulation signal using the electrode contacts of the ABI electrode array, and iv. determining a maximum response location on the patient brainstem where a largest afferent nerve signal is sensed. The ABI electrode array is then repositioned to the optimal placement location.

BRIEF DESCRIPTION OF THE DRAWINGS

FIG. 5 shows an example of an ABI electrode array.

DETAILED DESCRIPTION OF SPECIFIC EMBODIMENTS

Embodiments of the present invention determine an optimized placement location for an ABI electrode array by using both the afferent nerve fibers that forward elicited action potentials in the cochlea to the auditory brainstem, and the efferent nerve fibers that forward nerve signals from the brain stem to the cochlea. This approach for the first time allows the determination of an optimal placement location for an ABI electrode array by taking advantage of purely objective frequency resolved measurements (EABR is not frequency resolved).

Figure 1:
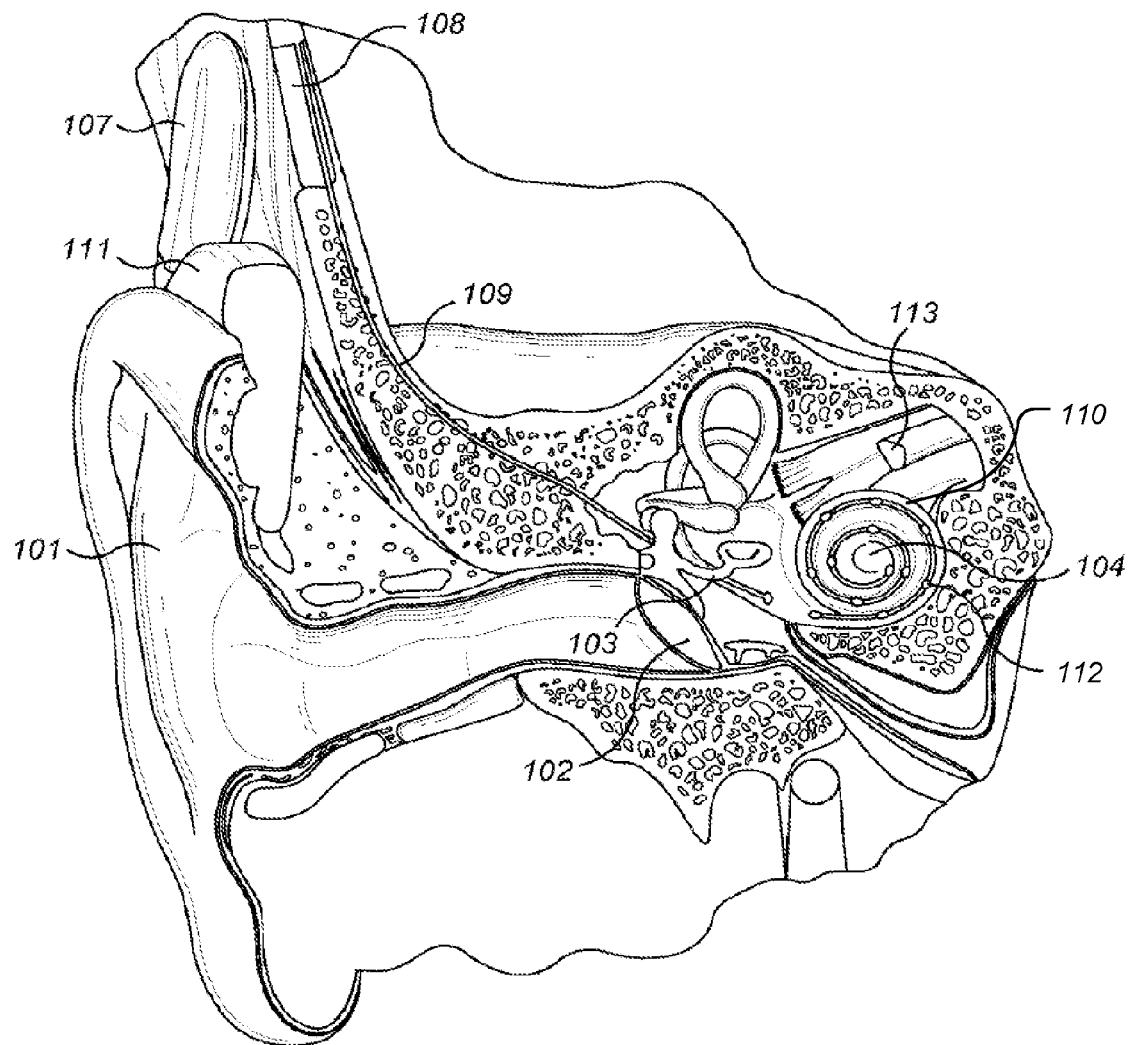
FIG. 1 shows a section view of a human ear with a typical cochlear implant system designed to deliver electrical stimulation to the inner ear.
Figure 2:
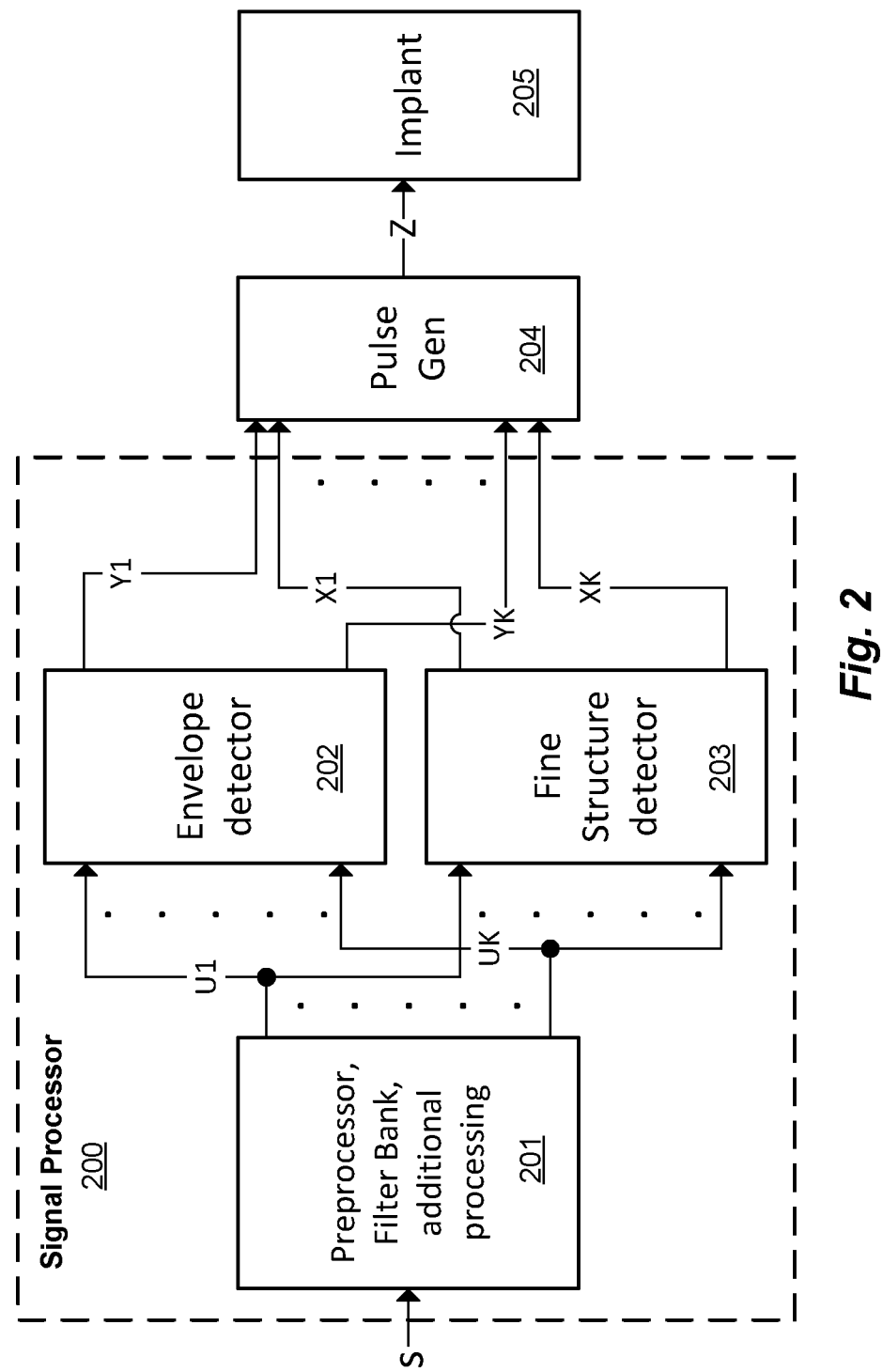
FIG. 2 shows various functional blocks in a signal processing arrangement for a hearing implant according to an embodiment of the present invention.
Figure 3:
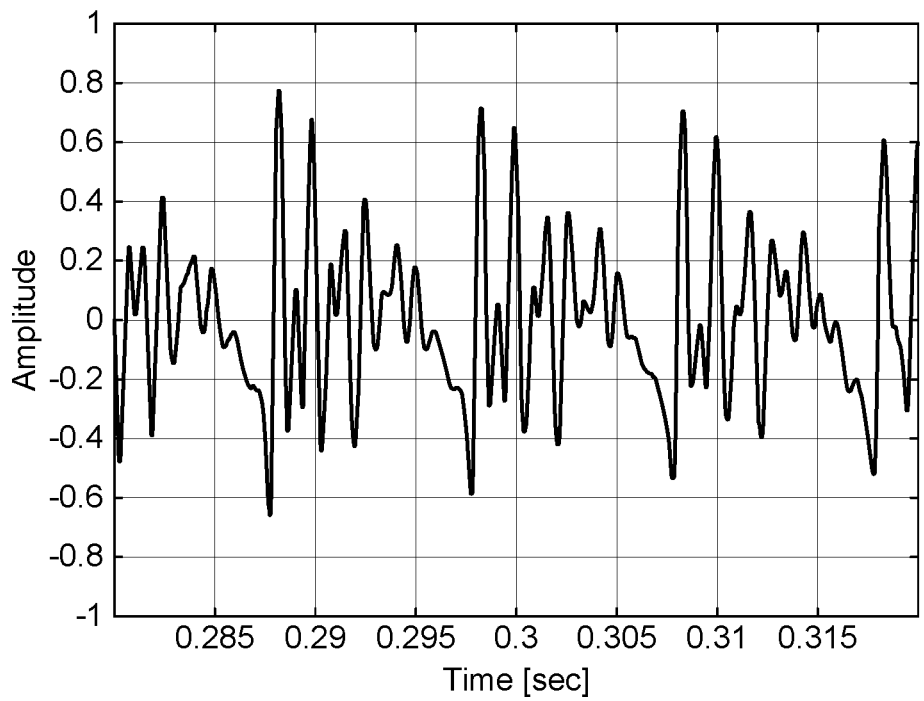
FIG. 3 shows an example of a short time period of an audio speech signal from a microphone.
Figure 4:
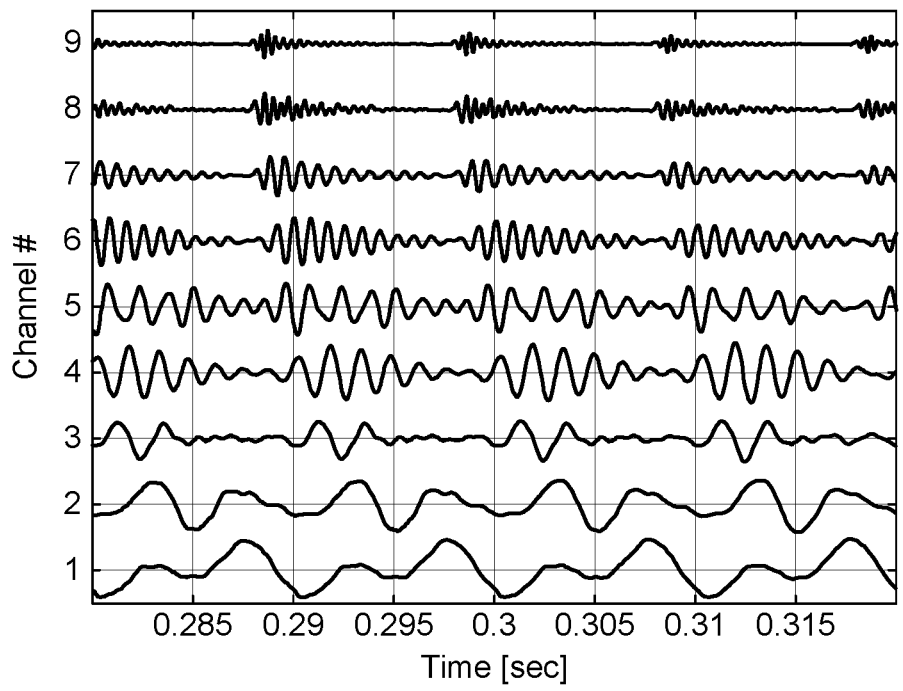
FIG. 4 shows an acoustic microphone signal decomposed by band-pass filtering by a bank of filters into a set of band pass signals.
Figure 6A:
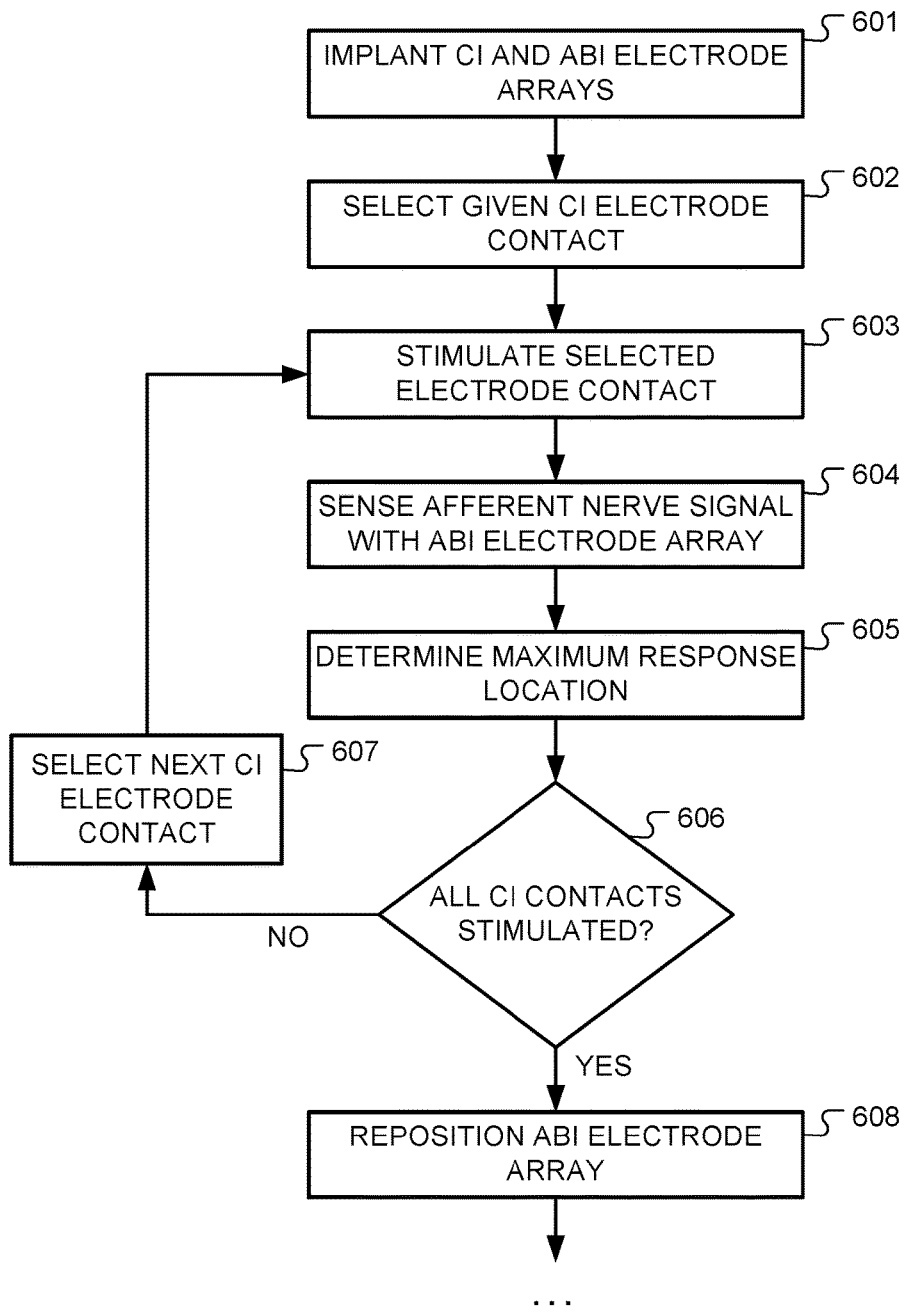
FIGS. 6A-6B show various logical steps in providing an optimal, placement location for an ABI electrode array using a cochlear implant according to an embodiment of the present invention.
Figure 6B:
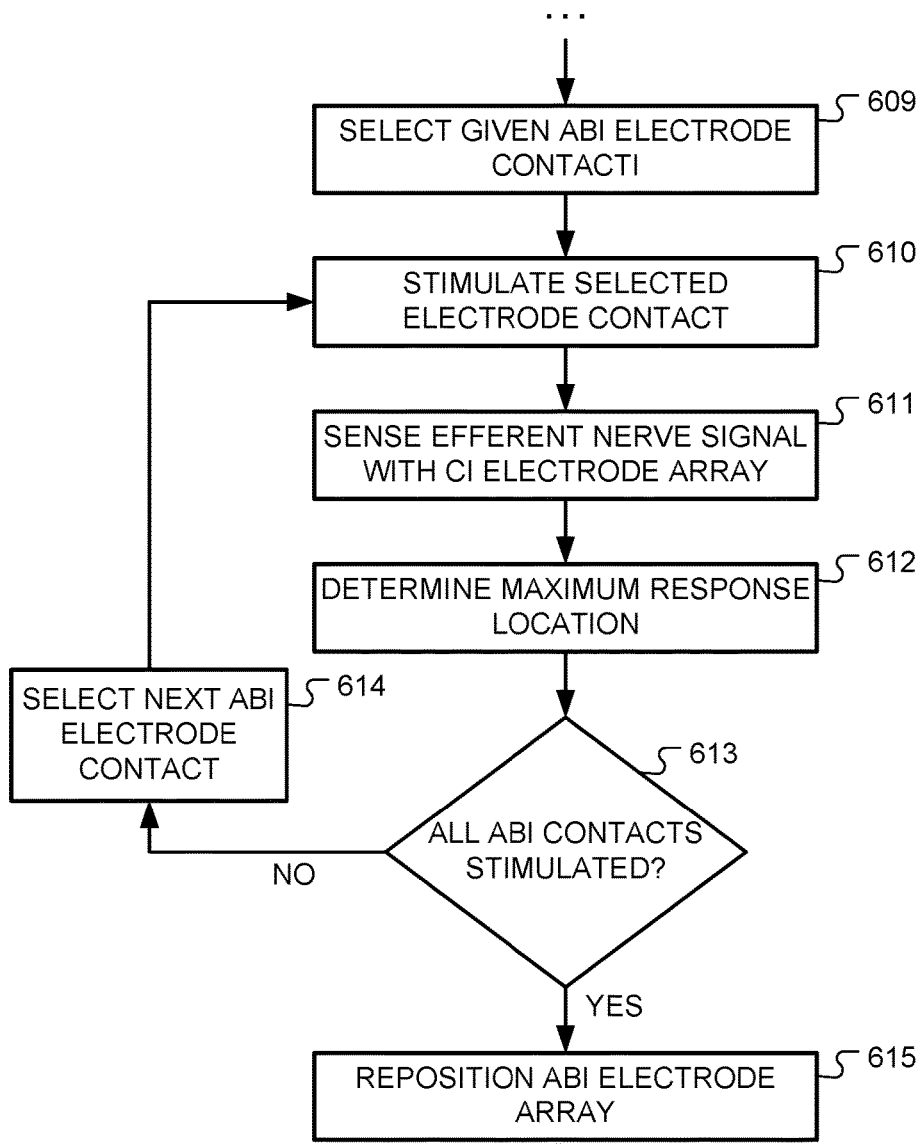

FIGS. 6A-6B show various logical steps in providing an optimal, placement location for an ABI electrode array according to an embodiment of the present invention. Embodiments of the invention may be implemented in part in any conventional computer programming language. For example, preferred embodiments may be implemented in a procedural programming language (e.g., "C") or an object oriented programming language (e.g., "C++", Python). A pseudo code example of such an arrangement can be set forth as:

```
Afferent Signal Processing:
    for selected CI contacts
        Stim(sel_contact)
        AfferentSense(ABI_contacts)
        MaxResponseLocation(ABI_contacts)
    reposition ABI electrode array
Efferent Signal Processing:
    for selected ABI contacts
        Stim(sel_contact)
        EfferentSense(CI_contacts)
        MaxResponseLocation(CI_contacts)
    reposition ABI electrode array
```

Alternative embodiments of the invention may be implemented as pre-programmed hardware elements, other related components, or as a combination of hardware and software components.

The process starts during a system implantation surgery conducted before the NF2 tumor is removed and before the auditory nerve is damaged. A cochlear implant (CI) electrode array and the ABI electrode array initially are implanted in the patient, step 601. Implantation of the CI electrode array is a normal surgical insertion process on the affected side (the side with the tumor). Implantation of the ABI electrode array is at an initial placement location on the affected side of the patient brainstem. Both electrode arrays include multiple electrode contacts that can be controlled by a single controller element; for example, a signal processor of a combined CI/ABI system, or by two separate but synchronized controllers and systems.

An improved placement location is then determined for the ABI electrode array an iterative stimulation process that uses some or all of the electrode contacts on the CI electrode array. For each of these electrode contacts, a specific electrode contact is selected, step 602, and a stimulation signal is delivered to the selected electrode contact, step 603. The stimulation signal delivered to the selected electrode contact may be a single electrical pulse, or a sequence of multiple electrical pulses.

The CI stimulation signal stimulates nerve action potentials within the cochlea that are transmitted via afferent nerve fibers to the brainstem. The electrode contacts of the ABI electrode array are configured to sense the afferent nerve signal response to the stimulation signal, step 604, and a maximum response location on the patient brainstem is determined where a largest afferent nerve signal is sensed, step 605. In some embodiments, sensing the afferent nerve signal response may include sensing a late elaboration of the afferent nerve signal response to the stimulation signal such as an electrically evoked auditory brainstem response (EABR) signal.

If all of the fitting contacts have not yet been used, step 606, the next CI electrode contact is selected, step 607, and the iterative stimulation process repeats, steps 603-606. The ABI electrode array is then repositioned to the improved placement location, step 608.

After determining an improved placement location for the ABI electrode array, steps 602-608, then the final optimal placement location is determined by a similar iterative process in the "other" direction. That is, for some or all of the electrode contacts on the ABI electrode array, a specific electrode contact of the ABI electrode array, is selected, step 609. A stimulation signal then is delivered to the selected electrode contact, step 610. The stimulation signal delivered to the selected electrode contact may be a single electrical pulse, or a sequence of multiple electrical pulses.

The ABI stimulation signal stimulates nerve action potentials within the brainstem that are transmitted via efferent nerve fibers to the cochlea. The electrode contacts of the CI electrode array are configured to sense the efferent nerve signal response to the stimulation signal, step 611, and a maximum response location in the patient cochlea is determined where a largest afferent nerve signal is sensed, step 612. If all of the ABI electrode contacts have not yet been used, step 613, the next ABI electrode contact is selected, step 614, and the iterative stimulation process repeats, steps 610-613. The ABI electrode array is then repositioned to the final optimized placement location, step 615.

If the maximum response locations in the cochlea do not sufficiently overlap with the corresponding tonotopic places of the electrode contacts of the CI electrode array, the ABI electrode array may be further repositioned and the entire procedure may be performed again. Once the sensed signals in the CI electrode array are focused sufficiently near the corresponding individual electrode contacts of the CI electrode, the placement of the ABI electrode array then has been identified that is both reproducible and optimal in terms of natural tonotopicity of the patient.

In some patients undesired stimulation effects may be caused by the stimulation signals delivered by the ABI electrode array (e.g. stimulation of the vagus nerve). Following the above process allows such adverse effects to be may be reduced or avoided altogether. If the delivery of a stimulus at a specific ABI electrode contact causes a visible reaction in the body of the anesthetized patient, then a different placement of that electrode contact may be identified which does not cause this reaction, but which still yields a comparable signal at the sensing electrode contact(s) in the cochlea.

In some specific embodiments, it may be possible to locate the ABI electrode array using only the ABI afferent sensing portion of the process (i.e., steps 602-608) or only the CI efferent sensing portion of the process (i.e., steps 610-615).

Once the ABI electrode array has been placed in an optimal location as determined by the above process, the tumor may be surgically removed. If the tumor removal entirely prohibits normal signal transmission via the acoustic nerve, then the patient must solely rely on the ABI stimulation, but at least there will be the benefit from an optimally placed ABI electrode array. In those circumstances, if separate CI and ABI systems were used for the intra-operative test process, then the CI system may be removed and the ABI system only remains implanted in the patient. In some cases a combined CI/ABI system may have been used, in which case the entire system may be left implanted, but only the ABI electrode contacts will be operated later during daily use of the system by the patient. If the auditory nerve still has some ability to transmit useful information from elicited action potentials in the cochlea to the auditory brainstem, then the patient may benefit from that, for which it is preferable to leave both systems or the combined CI/ABI system implanted. In a subsequent fitting session operation and stimulation parameters of the system may be chosen such that both portions of the system (CI and ABI) cooperate in order to yield the best output for the patient.

As mentioned above, either two separate CI and ABI systems may be used, or a single combined CI/ABI system may be used. In the case of separate systems, both processors need to be communicatively coupled to each other. During the intra-operative location testing, they need to exchange information in order to at least coordinate the stimulus and sensing timings in the respective systems. After surgery, during daily use of the hearing implant system by the patient, information still has to be exchanged between the CI and ABI systems to support coordinated stimulation. In the case of a combined CI/ABI, a system may be used such as is disclosed in U.S. Pat. No. 5,922,017 (incorporated herein by reference in its entirety), modified however such that one electrode branch comprises an electrode carrier with a paddle electrode at its distal end as known from state-of-the-art ABI. The specific number of electrode contacts both in the CI and ABI may be equal or different in both electrodes; for example, 12 each.

Rather than using a cochlear implant electrode array for positioning the ABI electrode array as described above, other embodiments of the present invention may use otoacoustic emissions. Specific such embodiments may be implemented in part in any conventional computer programming language. For example, preferred embodiments may be implemented in a procedural programming language (e.g., "C") or an object oriented programming language (e.g., "C++", Python). A pseudo code example of such an arrangement can be set forth as:

```
Acoustic Signal Processing:
    for selected CI contacts
        AcousticStim(sel_freq)
        AfferentSense(ABI_contacts)
        MaxResponseLocation(ABI_contacts)
    reposition ABI electrode array
Otoacoustic Emission Processing:
    for selected ABI contacts
        Stim(sel_contact)
        OAESense(freq, intensity)
    reposition ABI electrode array
```

Alternative embodiments of the invention may be implemented as pre-programmed hardware elements, other related components, or as a combination of hardware and software components.

Figure 7A:
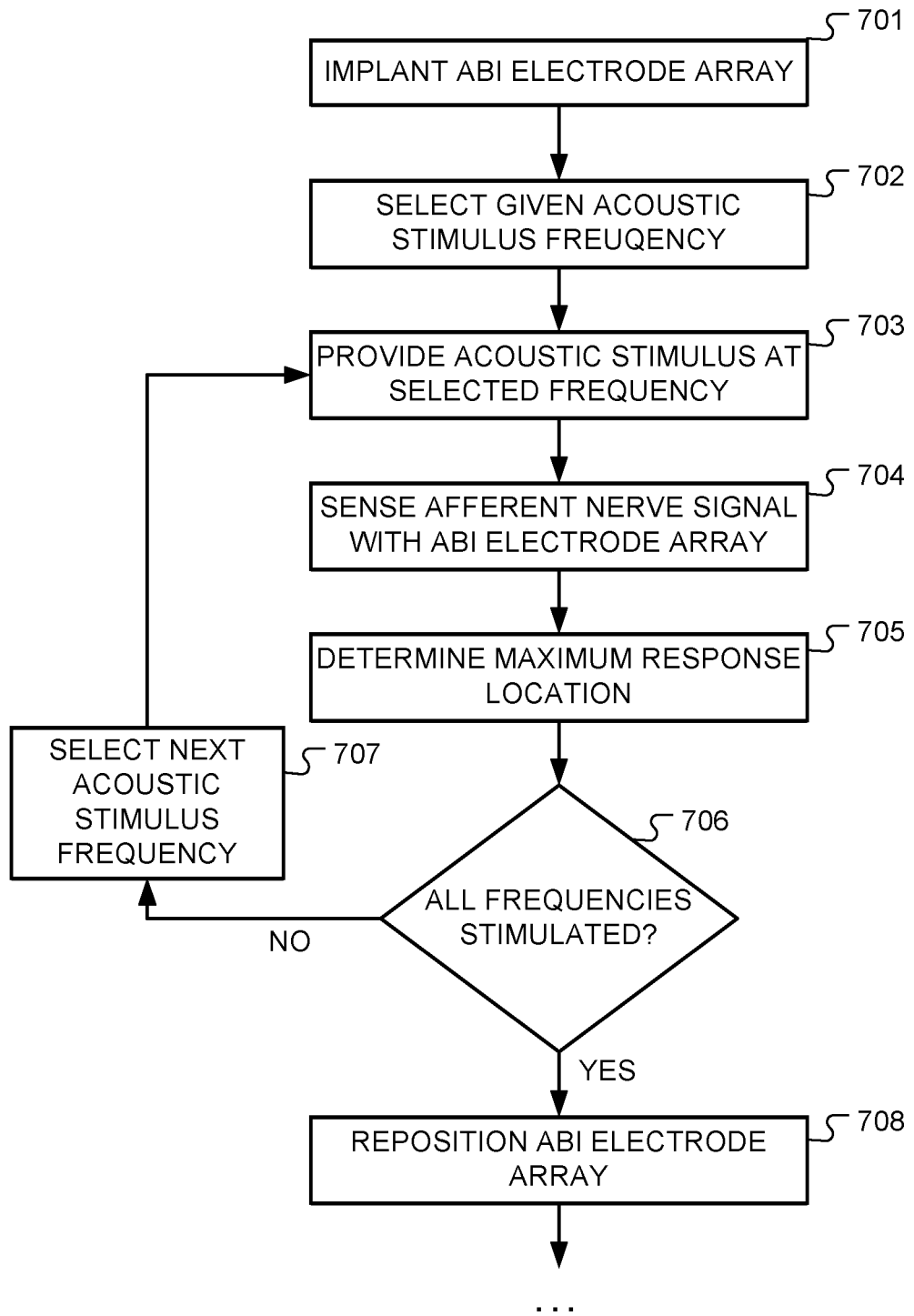
FIGS. 7A-7B show various logical steps in providing an optimal, placement location for an ABI electrode array using otoacoustic emissions according to an embodiment of the present invention.
Figure 7B:
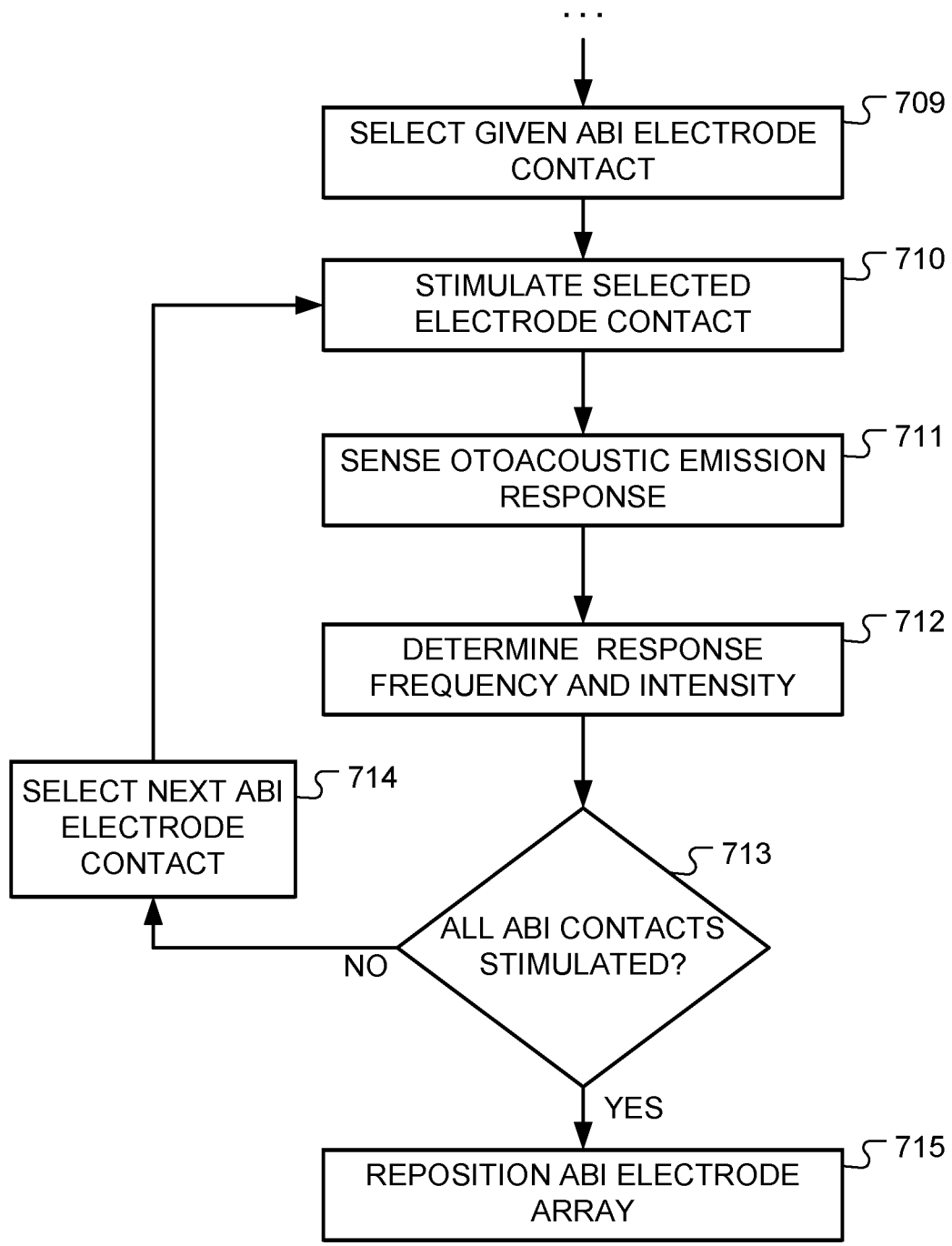

FIGS. 7A-7B show various logical steps in providing an optimal, placement location for an ABI electrode array according to an embodiment of the present invention that uses otoacoustic emissions. The process starts during a system implantation surgery conducted before the NF2 tumor is removed and before the auditory nerve is damaged. The ABI electrode array initially is implanted in the patient, step 701, on the affected side (the side with the tumor) of the patient brainstem.

An improved placement location is then determined for the ABI electrode array an iterative stimulation process that uses a range of acoustic stimulus frequencies. For each of a plurality of acoustic stimulus frequencies in the range, a specific acoustic stimulus frequency is selected, step 702, and a narrow-band acoustic stimulus is provided to the affected ear at the specific acoustic stimulus frequency, step 703. For example, the acoustic stimulus may specifically be a sine wave pure tone produced by a loudspeaker placed in the ear canal or in some more remote location. Of course, this only makes sense for a patient with some residual hearing, as is the case for most NF2 patients.

The acoustic stimulus signal stimulates nerve action potentials within the cochlea that are transmitted via afferent nerve fibers to the brainstem. The electrode contacts of the ABI electrode array are configured to sense the afferent nerve signal response to the acoustic stimulus, step 704, and a maximum response location on the patient brainstem is determined where a largest afferent nerve signal is sensed, step 705. If all of the acoustic stimulus frequencies in the desired testing range have not yet been used, step 706, the next acoustic stimulus frequency is selected, step 707, and the iterative stimulation process repeats, steps 703-706. The ABI electrode array is then repositioned to the improved placement location, step 708.

As a supplement (or alternative) to the foregoing frequency selective acoustic stimulus process, electrical stimulation may also be provided, for example, by an extra-cochlear stimulation electrode attached in the middle ear on or about the round window membrane. In such embodiments, sensing the afferent nerve signal response may include sensing a late elaboration of the afferent nerve signal response to the stimulation signal such as an electrically evoked auditory brainstem response (EABR) signal.

After determining an improved placement location for the ABI electrode array, steps 702-708, then the final optimal placement location is determined by a similar iterative process in the "other" neural pathway direction. That is, for some or all of the electrode contacts on the ABI electrode array, a specific electrode contact of the ABI electrode array, is selected, step 709. A stimulation signal then is delivered to the selected electrode contact, step 710. The stimulation signal delivered to the selected electrode contact may be a single electrical pulse, or a sequence of multiple electrical pulses.

The ABI stimulation signal stimulates nerve action potentials within the brainstem that are transmitted via efferent nerve fibers to peripheral nervous tissue (e.g., the hair cells) in the cochlea. The hair cells receiving these nerve signals move according to the received signal and produce otoacoustic emission signals, which may be recorded by a microphone located in the middle ear or the outer ear canal, step 711, and the frequency and intensity of the response may be determined, step 712. Because of the tonotopicity effect of the cochlea, the frequency of the otoacoustic emissions will depend on the location of the ABI electrode contact which provides the stimulation signal. If all of the ABI electrode contacts have not yet been used, step 713, the next ABI electrode contact is selected, step 714, and the iterative stimulation process repeats, steps 710-713. The ABI electrode array is then repositioned to the final optimized placement location, step 715.

Once an optimum or acceptable placement of the ABI electrode array has been identified, the procedure is finished. In this context, an optimum placement may be considered a placement such that the stimulus signals provided by the ABI electrode contacts cause otoacoustic emissions over a frequency range that reliably support speech understanding or music perception. Or the range may be defined in technical terms such as a range from about 200 Hz (or lower) to 4 kHz or 8 kHz. (where the limits will always depend on the actual hearing ability of the patient.)

In some patients undesired stimulation effects may be caused by the stimulation signals delivered by the ABI electrode array (e.g. stimulation of the vagus nerve). Following the above process allows such adverse effects to be may be reduced or avoided altogether. If the delivery of a stimulus at a specific ABI electrode contact causes a visible reaction in the body of the anesthetized patient, then a different placement of that electrode contact may be identified which does not cause this reaction, but which still yields a comparable signal at the sensing electrode contact(s) in the cochlea.

In some specific embodiments, it may be possible to locate the ABI electrode array using only the acoustic stimulus portion of the process (i.e., steps 702-708) or only the otoacoustic emissions sensing portion of the process (i.e., steps 710-715).

Once the ABI electrode array has been placed in an optimal location as determined by the above process, the tumor may be surgically removed. If the tumor removal entirely prohibits normal signal transmission via the acoustic nerve, then the patient must solely rely on the ABI stimulation, but at least there will be the benefit from an optimally placed ABI electrode array.

For the intra-operative ABI electrode placement testing, a system that includes both an ABI implant and a otoacoustic emission detection arrangement is needed. Both subsystems need to be controlled and timed so that they stimulate/measure in a coordinated manner.

If the auditory nerve retains some ability to transmit valuable information from elicited action potentials in the cochlea to the auditory brainstem, the patient may benefit from them, especially in that the cochlea of the patient remains completely untouched, so that any residual hearing function is preserved from which the patient may continue to benefit.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for determining an optimal placement location for an auditory brainstem implant (ABI) electrode array having a plurality of electrode contacts configured for delivering electrical stimulation signals, the method comprising:

inserting into a patient cochlea a cochlear implant (CI) electrode array having a plurality of electrode contacts configured for delivering electrical stimulation signals to adjacent neural tissue;

initially placing the ABI electrode array at an initial placement location on a patient brainstem;

determining an improved placement location for the ABI electrode array by, for a plurality of electrode contacts on the CI electrode array:

i. selecting a specific electrode contact of the CI electrode array, ii. delivering a stimulation signal to the selected electrode contact, iii. sensing an afferent nerve signal response to the stimulation signal using the electrode contacts of the ABI electrode array, and iv. determining a maximum response location on the patient brainstem where a largest afferent nerve signal is sensed;

repositioning the ABI electrode array to the improved placement location;

determining the optimal placement location for the ABI electrode array by, for a plurality of electrode contacts on the ABI electrode array:

i. selecting a specific electrode contact of the ABI electrode array,
ii. delivering a stimulation signal to the selected electrode contact,
iii. sensing an efferent nerve signal response to the stimulation signal using the electrode contacts of the CI electrode array, and
iv. determining a maximum response location in the patient cochlea where a largest efferent nerve signal is sensed; and
repositioning the ABI electrode array to the optimal placement location.

2. The method according to claim 1, further comprising:
reperforming the steps of determining the improved placement location and repositioning the ABI electrode array.

3. The method according to claim 1, further comprising:
reperforming the steps of determining the optimal placement location and repositioning the ABI electrode array.

4. The method according to claim 1, wherein the stimulation signal delivered to the selected electrode contact of the CI electrode array or the ABI electrode array comprises a single electrical pulse.

5. The method according to claim 1, wherein the stimulation signal delivered to the selected electrode contact of the CI electrode array or the ABI electrode array comprises a sequence of multiple electrical pulses.

6. The method according to claim 1, wherein determining the improved placement location for the ABI electrode array includes using all of the electrode contacts on the CI electrode array.

7. The method according to claim 1, wherein determining the optimal placement location for the ABI electrode array includes using all of the electrode contacts on the ABI electrode array.

8. The method according to claim 1, wherein sensing the afferent nerve signal response includes sensing a late elaboration of the afferent nerve signal response to the stimulation signal.

9. The method according to claim 8, wherein the late elaboration includes an electrically evoked auditory brainstem response (EABR) signal.

10. A non-transitory tangible computer-readable medium having instructions thereon for determining an optimal placement location for an auditory brainstem implant (ABI) electrode array having a plurality of electrode contacts configured for delivering electrical stimulation signals, the instructions comprising:
program code for determining an improved placement location for the ABI electrode array by, for a plurality of electrode contacts on a cochlear implant (CI) electrode array implanted in a patient cochlea and having the plurality of electrode contacts configured for delivering electrical stimulation signals to adjacent neural tissue:
i. selecting a specific electrode contact of the CI electrode array,
ii. delivering a stimulation signal to the selected electrode contact,
iii. sensing an afferent nerve signal response to the stimulation signal using the electrode contacts of the ABI electrode array, and
iv. determining the improved placement location based on a maximum response location on the patient brainstem where a largest afferent nerve signal is sensed; and program code for determining the optimal placement location for the ABI electrode array by, for a plurality of electrode contacts on the ABI electrode array:
i. selecting a specific electrode contact of the ABI electrode array,
ii. delivering a stimulation signal to the selected electrode contact,
iii. sensing an efferent nerve signal response to the stimulation signal using the electrode contacts of the CI electrode array, and
iv. determining the optimal placement location based on a maximum response location on the patient brainstem where a largest afferent nerve signal is sensed.

11. The computer readable medium according to claim 10, further comprising:
program code for reperforming the steps of determining the improved placement location and repositioning the ABI electrode array.

12. The computer readable medium according to claim 10, further comprising:
program code for reperforming the steps of determining the optimal placement location and repositioning the ABI electrode array.

13. The computer readable medium according to claim 10, wherein the stimulation signal delivered to the selected electrode contact of the CI electrode array or the ABI electrode array comprises a single electrical pulse.

14. The computer readable medium according to claim 10, wherein the stimulation signal delivered to the selected electrode contact of the CI electrode array or the ABI electrode array comprises a sequence of multiple electrical pulses.

15. The computer readable medium according to claim 10, wherein the program code for determining the improved placement location for the ABI electrode array includes program code for using all of the electrode contacts on the CI electrode array.

16. The computer readable medium according to claim 10, wherein the program code for determining the optimal placement location for the ABI electrode array includes program code for using all of the electrode contacts on the ABI electrode array.

17. The computer readable medium according to claim 10, wherein sensing the afferent nerve signal response includes sensing a late elaboration of the afferent nerve signal response to the stimulation signal.

18. The computer readable medium according to claim 17, wherein the late elaboration includes an electrically evoked auditory brainstem response (EABR) signal.

19. A method for determining an optimal placement location for an auditory brainstem implant (ABI) electrode array having a plurality of electrode contacts configured for delivering electrical stimulation signals, the method comprising:
initially placing the ABI electrode array at an initial placement location on a patient brainstem;
determining an improved placement location for the ABI electrode array by, for a plurality of acoustic stimulus frequencies:
i. selecting a specific acoustic stimulus frequency,
ii. delivering an acoustic stimulus at the selected acoustic stimulus frequency,
iii. sensing an afferent nerve signal response to the acoustic stimulus using the electrode contacts of the ABI electrode array, and iv. determining a maximum response location on the patient brainstem where a largest afferent nerve signal is sensed;
repositioning the ABI electrode array to the improved placement location;
determining the optimal placement location for the ABI electrode array by, for a plurality of electrode contacts on the ABI electrode array:
  i. selecting a specific electrode contact of the ABI electrode array,
  ii. delivering a stimulation signal to the selected electrode contact, and
  iii. sensing an otoacoustic emission response to the stimulation signal, and
  iv. determining a frequency and intensity of the otoacoustic emission response; and
repositioning the ABI electrode array to the optimal placement location.

20. A non-transitory tangible computer-readable medium having instructions thereon for determining an optimal placement location for an auditory brainstem implant (ABI) electrode array having a plurality of electrode contacts configured for delivering electrical stimulation signals, the instructions comprising:

program code for determining an improved placement location for the ABI electrode array by, for a plurality of acoustic stimulus frequencies:
  i. selecting a specific acoustic stimulus frequency,
  ii. delivering an acoustic stimulus at the selected acoustic stimulus frequency,
  iii. sensing an afferent nerve signal response to the acoustic stimulus using the electrode contacts of the ABI electrode array, and
  iv. determining the improved placement location based on a maximum response location on the patient brainstem where a largest afferent nerve signal is sensed; and
program code for determining the optimal placement location for the ABI electrode array by, for a plurality of electrode contacts on the ABI electrode array:
  i. selecting a specific electrode contact of the ABI electrode array,
  ii. delivering a stimulation signal to the selected electrode contact,
  iii. sensing an otoacoustic emission response to the stimulation signal, and
  iv. determining a frequency and intensity of the otoacoustic emission response.

* * * * *